United States Patent
Corl et al.

(10) Patent No.: US 9,257,226 B2
(45) Date of Patent: Feb. 9, 2016

(54) ROTARY TRANSFORMER AND ASSOCIATED DEVICES, SYSTEMS, AND METHODS FOR ROTATIONAL INTRAVASCULAR ULTRASOUND

(71) Applicant: Volcano Corporation, San Diego, CA (US)

(72) Inventors: Paul Douglas Corl, Palo Alto, CA (US); David Miller, Bradford, MA (US)

(73) Assignee: VOLCANO CORPORATION, San Diego, CA (US)

( * ) Notice: Subject to any disclaimer, the term of this patent is extended or adjusted under 35 U.S.C. 154(b) by 0 days.

(21) Appl. No.: 14/695,946

(22) Filed: Apr. 24, 2015

(65) Prior Publication Data
US 2015/0228406 A1    Aug. 13, 2015

Related U.S. Application Data

(62) Division of application No. 13/847,300, filed on Mar. 19, 2013, now Pat. No. 9,022,934.

(60) Provisional application No. 61/612,749, filed on Mar. 19, 2012.

(51) Int. Cl.
| | |
|---|---|
| *H01F 27/28* | (2006.01) |
| *H01F 38/18* | (2006.01) |
| *A61B 8/12* | (2006.01) |
| *H01F 41/02* | (2006.01) |
| *A61B 8/00* | (2006.01) |

(52) U.S. Cl.
CPC *H01F 38/18* (2013.01); *A61B 8/12* (2013.01); *A61B 8/445* (2013.01); *A61B 8/4461* (2013.01); *A61B 8/56* (2013.01); *H01F 27/2804* (2013.01);

(Continued)

(58) Field of Classification Search
CPC .......... H01F 27/00–27/36; H01F 21/00–21/10
USPC .......................... 336/130–136, 180–184, 200
See application file for complete search history.

(56) References Cited

U.S. PATENT DOCUMENTS

| | | | |
|---|---|---|---|
| 4,755,783 A | * | 7/1988 | Fleischer ............ H01F 17/0006 336/180 |
| 5,243,988 A | | 9/1993 | Sieben et al. |

(Continued)

FOREIGN PATENT DOCUMENTS

| | | |
|---|---|---|
| JP | 07-115783 A | 5/1995 |
| KR | 10-0177232 B1 | 4/1999 |

OTHER PUBLICATIONS

International Searching Authority/KIPO, "Notification of Transmittal of the International Search Report and the Written Opinion of the International Searching Authority, or the Declaration," for PCT/US2013/032832, mailed Jul. 8, 2013, 9 pages.

*Primary Examiner* — Tuyen Nguyen
(74) *Attorney, Agent, or Firm* — Haynes and Boone LLP (57) ABSTRACT

Rotational intravascular ultrasound (IVUS) imaging devices, systems, and methods are provided. The present disclosure is particularly directed to rotary transformers incorporating flex circuits that are suitable for use in rotational IVUS systems. In one embodiment, a rotary transformer for a rotational IVUS device includes: a rotational component and a stationary component. At least one of the rotational and stationary components includes a core formed of a magnetically conductive material and a flex circuit coupled to the core. In some instances, the flex circuit is coupled to the core such that a coil portion of the flex circuit is received within a recess of the core and an extension of the flex circuit extending from the coil portion extends through an opening of the core.

27 Claims, 8 Drawing Sheets

(52) U.S. Cl.
CPC ............ *H01F 27/2885* (2013.01); *H01F 41/02* (2013.01); *Y10T 29/49073* (2015.01)

(56) References Cited

U.S. PATENT DOCUMENTS

| | | |
|---|---|---|
| 5,546,948 A | 8/1996 | Hamm et al. |
| 6,426,852 B1 | 7/2002 | Chi |
| 8,007,440 B2 | 8/2011 | Magnin et al. |
| 2002/0014942 A1* | 2/2002 | Harding .............. H01F 27/2804 336/212 |
| 2005/0034541 A1 | 2/2005 | Koyama et al. |
| 2008/0180279 A1* | 7/2008 | Hoerl ................... B23Q 1/0009 340/870.31 |
| 2010/0234736 A1 | 9/2010 | Corl |

* cited by examiner

ROTARY TRANSFORMER AND ASSOCIATED DEVICES, SYSTEMS, AND METHODS FOR ROTATIONAL INTRAVASCULAR ULTRASOUND

CROSS-REFERENCE TO RELATED APPLICATIONS

This application is a divisional application of U.S. application Ser. No. 13/847,300 filed on Mar. 19, 2013, now U.S. Pat. No. 9,022,934, which claims priority to and the benefit of U.S. Provisional Patent Application No. 61/612,749 filed Mar. 19, 2012, which are hereby incorporated by reference in their entirety.

TECHNICAL FIELD

The present disclosure relates generally to intravascular ultrasound imaging inside the living body and, in particular, to an intravascular ultrasound imaging catheter that relies on a mechanically-scanned or rotated ultrasound transducer. Some embodiments are particularly directed to rotary transformers and associated devices, systems, and methods suitable for rotational intravascular ultrasound.

BACKGROUND

Intravascular ultrasound (IVUS) imaging is widely used in interventional cardiology as a diagnostic tool for a diseased vessel, such as an artery, within the human body to determine the need for treatment, to guide the intervention, and/or to assess its effectiveness. IVUS imaging uses ultrasound echoes to create an image of the vessel of interest. Ultrasound waves pass easily through most tissues and blood, but they are partially reflected from discontinuities arising from tissue structures (such as the various layers of the vessel wall), red blood cells, and other features of interest. The IVUS imaging system, which is connected to the IVUS catheter by way of a patient interface module (PIM), processes the received ultrasound echoes to produce a cross-sectional image of the vessel where the catheter is placed.

There are two types of IVUS catheters in common use today: rotational and solid-state, with each having advantages and disadvantages. The rotational IVUS catheter typically incorporates a rotating transducer element to direct an ultrasound beam in different directions in order to collect the echo data required to form an image, and a rotary transformer or other rotating electromechanical interface is needed to provide an electrical connection in order to maintain communication between the IVUS imaging system and the rotating transducer element. In contrast, the solid-state IVUS catheter uses electronic circuitry to steer an ultrasound beam in different directions, and hence it does not require a rotary transformer or other rotating electromechanical interface.

In a typical rotational IVUS catheter, a single ultrasound transducer element is located near the tip of a flexible driveshaft that spins inside a plastic sheath inserted into the vessel of interest. The fluid-filled sheath protects the vessel tissue from the spinning driveshaft while permitting ultrasound signals to freely propagate from the transducer into the tissue and back. In a side-looking IVUS device, the transducer element is oriented such that the ultrasound beam propagates generally perpendicular to the axis of the catheter. In a forward-looking IVUS device, the transducer element is oriented such that the ultrasound beam propagates distally from the tip at an oblique angle relative to the axis of the catheter. In either case, as the driveshaft rotates (typically at up to 30 revolutions per second), the transducer is periodically excited with a high voltage pulse to emit a short burst of ultrasound. Immediately following the ultrasound transmit burst, the transducer listens for the returning echoes reflected from various tissue structures, and the IVUS imaging system assembles a two-dimensional display of the vessel cross-section from a sequence of several hundred of these pulse/acquisition cycles occurring during a single revolution of the transducer/driveshaft.

Typically, the rotational IVUS catheter includes a driveshaft disposed within the catheter body, with the ultrasound transducer attached near the distal tip of the driveshaft. A single element piezoelectric transducer requires only two electrical leads, with this single pair of leads delivering the intermittent electrical transmit pulses to the transducer, and returning the received echo signals from the transducer to the receiver amplifier during the intervals between transmit pulses. The IVUS catheter is coupled to an interface module, which typically controls the rotation of the drive shaft within the catheter body and contains the transmitter and receiver circuitry. Since the catheter driveshaft and transducer are spinning (in order to scan a cross-section of the artery) and the transmitter/receiver circuitry is stationary within the interface module, an electromechanical interface must be provided where the electrical signal traverses the rotating mechanical junction. As commonly implemented in rotational IVUS imaging systems and further described in one the present applicant's previous patent application, U.S. Patent Publication Application No. 2010/0234736 A1, filed on Mar. 11, 2009, which is hereby incorporated by reference in its entirety, this can be accomplished via a rotary transformer that comprises two halves, separated by a narrow air gap that permits electrical coupling between the primary and secondary windings of the transformer while allowing relative motion (rotation) between the two halves. The spinning element (transducer, electrical leads, and driveshaft) is attached to the spinning portion of the rotary transformer, while the stationary transmitter and receiver circuitry contained in the interface module are attached to the stationary portion of the rotary transformer. This allows the transmit pulses to be delivered to the transducer and the received echo signals from the transducer to be return across the rotating interface to the imaging system by way of a patient interface module (PIM). The IVUS imaging system then processes the echo signals and assembles the data into a cross-sectional image of the vessel.

Current rotational IVUS PIMs typically incorporate a rotary transformer constructed from hand-wound wire coils. With these hand-wound coils, it is difficult to precisely control the geometry of the coils and the alignment of coils between the two halves of the rotary transformer. These difficulties translate into transformers that are expensive and complex to manufacture, suffer from poor coupling efficiency and/or narrow bandwidth, and exhibit significant variability among devices. This variability among transformers leads to inconsistent performance for the associated IVUS imaging systems, and the poor coupling efficiency and/or narrow transformer bandwidth degrades the image quality that should theoretically be available from the IVUS imaging system. Further, due to the complexity and expense of manufacturing traditional transformers, they do not lend themselves to disposable or one-time use applications.

While existing rotary transformers used with conventional rotational IVUS catheters deliver useful diagnostic information, there is a need for an improved rotary transformer design with improved coupling efficiency and wider bandwidth to provide greater signal-to-noise ratio and increased depth of penetration for more refined insight into the vessel condition.

Furthermore, there is a need for a consistent, low-cost method for manufacturing rotary transformers to support the particular needs of IVUS applications where the rotary transformer is included as a part of the sterile, disposable IVUS catheter assembly. Accordingly, there remains a need for improved electromechanical interfaces for use in rotational intravascular ultrasound systems.

SUMMARY

Embodiments of the present disclosure provide improved electromechanical interfaces for use in rotational intravascular ultrasound systems. In some particular embodiments, the electromechanical interfaces are rotary transformers that utilize a flex circuit.

In one embodiment, a rotary transformer for a rotational intravascular ultrasound (IVUS) device is provided. The rotary transformer includes a rotational component configured to be fixedly secured to a rotating portion of the rotational IVUS device such that the rotational component rotates with the rotating portion of the rotational IVUS device and a stationary component positioned adjacent to the rotational component such that when the rotational component rotates with the rotating portion of the rotational IVUS device the rotational component rotates relative to the stationary component. The rotational component includes a core formed of a magnetically conductive material and a flex circuit coupled to the core. The core has a front surface and a back surface, wherein the front surface includes a recessed surface portion that is recessed relative to surrounding portions of the front surface to define a recess. An opening extends through the core from the recessed surface portion to the back surface. The flex circuit includes a coil portion and an elongated extension extending from the coil portion. The flex circuit is coupled to the core such that the coil portion is received within the recess of the front surface of the core and the elongated extension extends through the opening extending through the core from the recessed surface portion to the back surface. The stationary component includes a core formed of a magnetically conductive material and a coil coupled to the core such that the coil portion of the flex circuit of the rotational component and the coil of the stationary component are configured to inductively communicate signals between one another.

In another embodiment, a rotational intravascular ultrasound (IVUS) imaging system is provided. The system includes an imaging device having a flexible elongate body having a proximal portion, a distal portion, and a lumen extending along a length of the flexible elongate body between the proximal and distal portions and an imaging element secured to a rotating element positioned within the lumen of the flexible elongate body. The imaging element is configured to be rotated relative to the flexible elongate body with the rotational element. A drive assembly is coupled to the proximal portion of the flexible elongate body. The drive assembly is configured to impart rotation on the rotational element. The drive assembly includes a rotary transformer. The rotary transformer includes a rotational component configured to be fixedly secured to a rotating portion of the rotational IVUS device such that the rotational component of the transformer rotates with the rotating portion of the rotational IVUS device and a stationary component of the transformer positioned adjacent to the rotational component such that when the rotational component of the transformer rotates with the rotating portion of the rotational IVUS device the rotational component of the transformer rotates relative to the stationary component of the transformer. The rotational component of the transformer includes a core formed of a magnetically conductive material and a flex circuit coupled to the core. The core has a front surface and a back surface, wherein the front surface includes a recessed surface portion that is recessed relative to surrounding portions of the front surface to define a recess. An opening extends through the core from the recessed surface portion to the back surface. The flex circuit includes a coil portion and an elongated extension extending from the coil portion. The flex circuit is coupled to the core such that the coil portion is received within the recess of the front surface of the core and the elongated extension extends through the opening extending through the core from the recessed surface portion to the back surface. The stationary component of the transformer includes a core formed of a magnetically conductive material and a coil coupled to the core such that the coil portion of the flex circuit of the rotational component and the coil of the stationary component are configured to inductively communicate signals between one another.

In yet another embodiment, a method is provided. The method includes providing a first core formed of a magnetically conductive material and providing a first flex circuit. The first core has a front surface and a back surface, wherein the front surface includes a recessed surface portion that is recessed relative to surrounding portions of the front surface to define a recess. An opening extends through the first core from the recessed surface portion to the back surface. The first flex circuit includes a coil portion and an elongated extension extending from the coil portion. The method further includes coupling the first flex circuit to the first core such that the coil portion of the first flex circuit is received within the recess of the front surface of the first core and the elongated extension extends through the opening extending through the first core from the recessed surface portion to the back surface. In some instances, the method further comprises providing a second core formed of a magnetically conductive material and providing a second flex circuit. The second core also has a front surface and a back surface, wherein the front surface includes a recessed surface portion that is recessed relative to surrounding portions of the front surface to define a recess. An opening extends through the second core from the recessed surface portion to the back surface. The second flex circuit includes a coil portion and an elongated extension extending from the coil portion. The second flex circuit is coupled to the second core such that the coil portion of the second flex circuit is received within the recess of the front surface of the second core and the elongated extension extends through the opening extending through the second core from the recessed surface portion to the back surface. The method also includes positioning the first core with the first flex circuit coupled thereto adjacent the second core with the second flex circuit coupled thereto such that the front surface of the first core faces the front surface of the second core.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. Similarly, recitation of ranges of values herein is merely intended to serve as a shorthand method of referring individually to each separate value falling within the disclosed range. Accordingly, unless otherwise indicated herein, each separate value within the disclosed ranges is incorporated into the specification as if it were individually recited herein.

Turning now to the figures, representative illustrations of various aspects of an exemplary rotational intravascular ultrasound (IVUS) probe are shown therein. In that regard, the rotational IVUS probes of the present disclosure facilitate the use of ultrasound transducer technologies within a rotational IVUS probe sized and shaped for use within human vasculature. Accordingly, in some instances the rotational IVUS probes of the present disclosure may incorporate one or more features from the rotational IVUS devices described in U.S. Pat. No. 5,243,988, U.S. Pat. No. 5,546,948, and U.S. Pat. No. 8,007,440, each of which is hereby incorporated by reference in its entirety.

Figure 1:
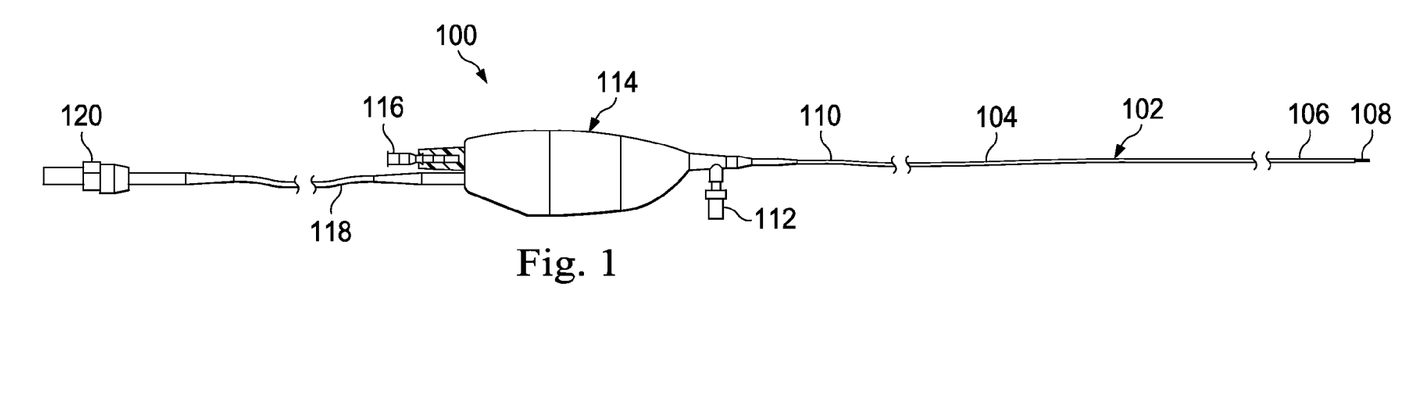
FIG. 1 is a diagrammatic schematic side view of an imaging device according to an embodiment of the present disclosure.

Referring now to FIG. 1, shown therein is a rotational IVUS device 100 according to an embodiment of the present disclosure. In that regard, the rotational IVUS device 100 includes a catheter 102 having a flexible elongate body 104 sized and shaped for insertion into a patient for diagnostic imaging. In some embodiments, the catheter 102 is sized and shaped for insertion into human vasculature. In that regard, the length of the flexible elongate body 104 is sized such that a distal portion 106 of the catheter can be positioned adjacent a point of interest within the patient. The distal portion 106 of the catheter 102 includes an ultrasound transducer 108. The ultrasound transducer(s) may be any type of suitable ultrasound transducer for imaging within a vessel of a patient and, in some particular embodiments, suitable for imaging within a blood vessel of a patient. Accordingly, in some instances, the ultrasound transducer is selected from the group of transducers consisting of lead-zirconate-titanate (PZT) piezoelectric transducers, PZT composite piezoelectric transducers, single crystal piezoelectric transducers, single crystal composite piezoelectric transducers, and/or other suitable piezoelectric material transducers.

The ultrasound transducer 108 is configured to be rotated about a longitudinal axis of the catheter 102. In some embodiments, the transducer is rotated at approximately 30 revolutions per second, while in other embodiments it may be rotated faster or slower. In some embodiments, the ultrasound transducer 108 is a single ultrasound transducer element secured to a distal portion of a flexible driveshaft that spins inside a lumen defined by an outer sheath of the catheter 102. In some embodiments, the ultrasound transducer element is oriented such that the ultrasound beam propagates at an oblique angle to the longitudinal axis of the catheter in a distal direction, such that the IVUS catheter is a forward-looking device. In some such forward looking embodiments, the oblique angle is between 30 degrees and 70 degrees, with an angle of approximately 50 degrees in one preferred embodiment. In other instances, the ultrasound transducer element is oriented such that the ultrasound beam propagates generally perpendicular to the longitudinal axis of the catheter, such that the IVUS catheter is a side looking device. In some such side-looking embodiments, the ultrasound beam propagates at an angle within +/−20 degrees of a perpendicular to the longitudinal axis of the catheter. In some embodiments, the fluid-filled outer sheath of the catheter 102 ends short of the ultrasound transducer such that the transducer element is directly exposed to the surrounding environment (e.g., blood, tissue, etc.). In some embodiments, the fluid-filled sheath extends beyond the ultrasound transducer element and fully protects the surrounding vessel tissue from the spinning transducer and driveshaft while permitting ultrasound signals to freely propagate from the transducer, through the sheath, into the tissue, and back. In that regard, a distal portion of the sheath is transparent to the ultrasound beam generated by the ultrasound transducer to facilitate sending and receiving the ultrasound signals and echoes.

In the aforementioned rotational IVUS catheter embodiments, as the transducer is rotated, it is periodically excited with a high voltage pulse to emit a short burst of ultrasound energy. Typically, the same transducer then listens for the returning echoes reflected from various tissue structures traversed by the ultrasound beam. The echo signals are amplified and processed by an IVUS image processing system coupled to the catheter, and the IVUS imaging system assembles a multitude of these processed echo signals into a cross-sectional display of the vessel.

A proximal portion 110 of the catheter 102 is coupled to a port 112. In some instances, the port 112 is a flush port through which saline, contrast media, or other suitable fluid is injected through the catheter 102 and into the blood vessel. In some embodiments, the port 112 is a luer lock flushing port that is in fluid communication with an inner lumen of the catheter in which the imaging element 108 and associated drive shaft are received. In that case, saline provides a biocompatible lubricant for the rotating driveshaft within the inner lumen of the catheter.

The proximal portion 110 of the catheter 102 is also coupled to a drive assembly 114. An extension 116 and a communication cable 118 extend proximally from the drive assembly 114. In that regard, communication cable 118 is coupled to a connector 120 that is configured to interface with an interface module of the IVUS imaging system. For example, in some instances the connector 120 plugs into the interface module. In some instances, the connector 120 is configured to interface with a patient interface module (PIM) that is in turn communicatively coupled to a separate processing unit or console of the IVUS imaging system. In other instances, the connector 120 is configured to interface directly with the processing unit or console of the IVUS imaging system.

In the embodiment illustrated in FIG. 1, the catheter 102 and drive assembly 114 comprise an over-the-wire device wherein the drive shaft is configured to receive (or be placed over) a guidewire, with the drive shaft rotating around the guidewire. In that regard, the inner lumen of the drive shaft that receives the guidewire is also lubricated in some instances, for example, using saline or other suitable biocompatible lubricant. Because the catheter 102 with its associated drive assembly 114 comprise an over-the-wire device, the components of that device, including the rotary transformer, are likely to come into contact with the sterile guidewire, either directly or indirectly (by way of fluid contact or contact with other items located within the sterile field). Since the rotary transformer may come into contact with sterile items, the rotary transformer itself needs to be sterile in order to prevent contamination of the guidewire and other items within the sterile field. Accordingly, embodiments of the rotary transformer(s) of the present disclosure discussed below are configured to be manufactured at low-cost such that they are suitable for use in disposable or one-time use situations while still providing wide bandwidth and high efficiency for a high quality ultrasound imaging. In that regard, in some instances the rotary transformers of the present disclosure are implemented in a drive assembly or PIM that is disposable or configured for a single use. It is understood, however, that embodiments of the present disclosure are suitable for use with rapid exchange and/or other non-over-the-wire types of catheters. For example, in some embodiments the rotary transformers are implemented for permanent use within PIMs that may or may not be positioned within the sterile field of an operating room.

Figure 2:
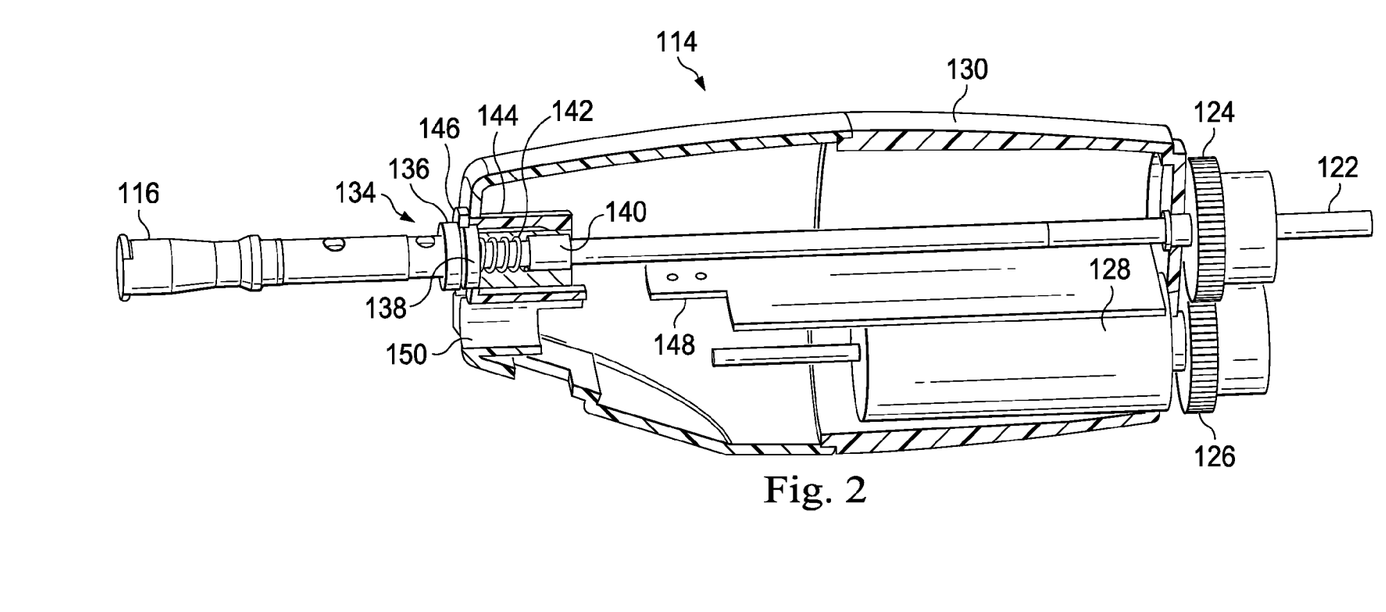
FIG. 2 is a diagrammatic, partial cutaway perspective side view of a drive assembly of the imaging device of FIG. 1 according to an embodiment of the present disclosure.

Referring now to FIG. 2, additional aspects of the drive assembly 114 will be described. In that regard, a drive shaft or drive cable 122 is coupled to a pair of gears 124 and 126. The imaging element 108 is coupled to a distal portion of the drive shaft or drive cable 122 such that rotation of the drive shaft or drive cable 122 also imparts rotation to the imaging element 108. To that end, the gear 126 is coupled to a motor 128 positioned within a housing 130. Rotational motion imparted on the gear 126 by motor 128 is passed to gear 124 that meshes with gear 126. Gear 124 is secured to drive shaft or drive cable 122 such that rotation of gear 124 causes rotation of drive shaft or drive cable 122 and, in turn, imaging element 108. A position encoder is coupled to the motor 128 in order to track and/or control rotation of the motor thereby controlling the rotation of the imaging element 108 to facilitate ultrasound imaging of a vessel.

In some instances, the rotation of the imaging element 108 within the catheter 102 is controlled by the interface module or other controller that the drive assembly is communicatively coupled to. The interface module also communicates with the imaging element 108 by sending and receiving electrical signals to and from the imaging element 108 via wires extending along the length of the catheter 102. In some embodiments, the wires extend within the drive shaft or drive cable 122. In that regard, in some instances there are two conductors, three conductors, or four conductors extending along the length of the catheter 102 to the imaging element 108. The interface module can receive, analyze, and/or display information received through the drive assembly 114 and/or pass the information on to additional components for processing and/or display. It is appreciated that any suitable functionality, controls, information processing and analysis, and display can be incorporated into the interface module and/or other components communicatively coupled to the interface module. In that regard, it is necessary for signals to be communicated between the stationary interface module and the rotating imaging element 108.

In that regard, transducer technologies require two or more conductive signal lines to facilitate operation of the imaging element 108. In order to pass the necessary signals, a suitable structure is needed to transmit electrical signals across the boundary between the rotating and stationary mechanical components. Particularly for ultrasound signals, the mode of transmission must maintain signal quality, without added noise or excessive distortion of the frequency response, sufficient for the interface module in conjunction with the IVUS system to produce a high quality image of the target tissue from the ultrasound echo signals. It will be appreciated that any suitable signals can be communicated across the boundary between the rotating and stationary mechanical components including, but not limited to electrical power, control signals, transmit pulses, and low amplitude ultrasound echo signals. The signal transfer across the boundary between the rotating and stationary mechanical components can occur at a high frequency and with a wide frequency response. The rotary transformers of the present disclosure described below are particularly suited to facilitate such communication of signals across the boundary of rotating and stationary components.

Referring again to FIG. 2, the drive assembly 114 includes a rotary transformer 134 that is configured to facilitate communication between the rotating and stationary components of the imaging system. In that regard, the rotary transformer 134 includes a rotating portion 136 and a stationary portion 138. Various aspects of rotary transformers suitable for use as rotary transformer 134 are described below with respect to FIGS. 3-12. Generally, each half of the rotary transformer 134 includes a coil or winding that is layered into an annular groove or recess of a core component. In some instances, the coil or winding includes two, three, four, five, or six turns. However, in other instances the coil or winding includes greater or fewer turns, including partial turns. As discussed below, in some specific embodiments of the present disclosure, the coil or winding is formed on a flex circuit. In that regard, transformer performance can be improved by minimizing the gap between the rotating portion 138 and the stationary portion 136 of the transformer 134 and placing the coils or windings of each portion 136 and 138 as close as possible to each other. Use of a flex circuit can facilitate minimizing the spacing between the rotating portion 138 and the stationary portion 136 and their corresponding coils/windings. In that regard, the closer spacing provides better coupling that facilitates higher efficiency and wider bandwidth as compared to a conventional rotary transformer. Further, the conductive lines or traces on the flex circuit rotary transformers of the present disclosure have a reduced skin effect as compared to coils formed from wire having a round or circular cross-sectional profile, further increasing the efficiency of the transformers of the present disclosure relative to that of a conventional transformer.

In the illustrated embodiment, a bearing 140 and spring 142 positioned within collar 144 maintain the stationary portion 138 in close proximity to the rotating portion 136. In that regard, the spring 142 urges the stationary portion 138 proximally (to left as viewed in FIG. 2) towards rotating portion 136. A flange 146 of the collar 144 abuts the outer surface of the housing 130 as shown. The rotating portion 136 is secured to the drive shaft or drive cable 122, either directly or indirectly, such that the rotating portion 136 rotates with the drive shaft/cable 122. For example, in some instances the rotating portion 136 is fixedly secured to the extension 116, which is, in turn, fixedly secured to the drive shaft/cable 122. The stationary portion 138 is communicatively coupled to a printed circuit board 148 contained within the housing 130. In that regard, in some embodiments leads coupled to the coil/winding of the stationary portion 138 are soldered to a portion of the printed circuit board 148. For example, in some instances the leads are soldered to the printed circuit board 148 such that they are in communication with a preamp or other processing component configured to condition signals. In that regard, in some instances one or more conductors of the cable 118 are coupled to the printed circuit board 148 (or a component coupled thereto) to receive the signals from the stationary portion 138. The cable 118 and its conductors extend through opening 150 and on to connector 120 in some embodiments. While portion 136 is the rotating portion and portion 138 is the stationary portion in the illustrated embodiment, in other arrangements, portion 136 is the stationary portion and portion 138 is the rotating portion.

Figure 3:
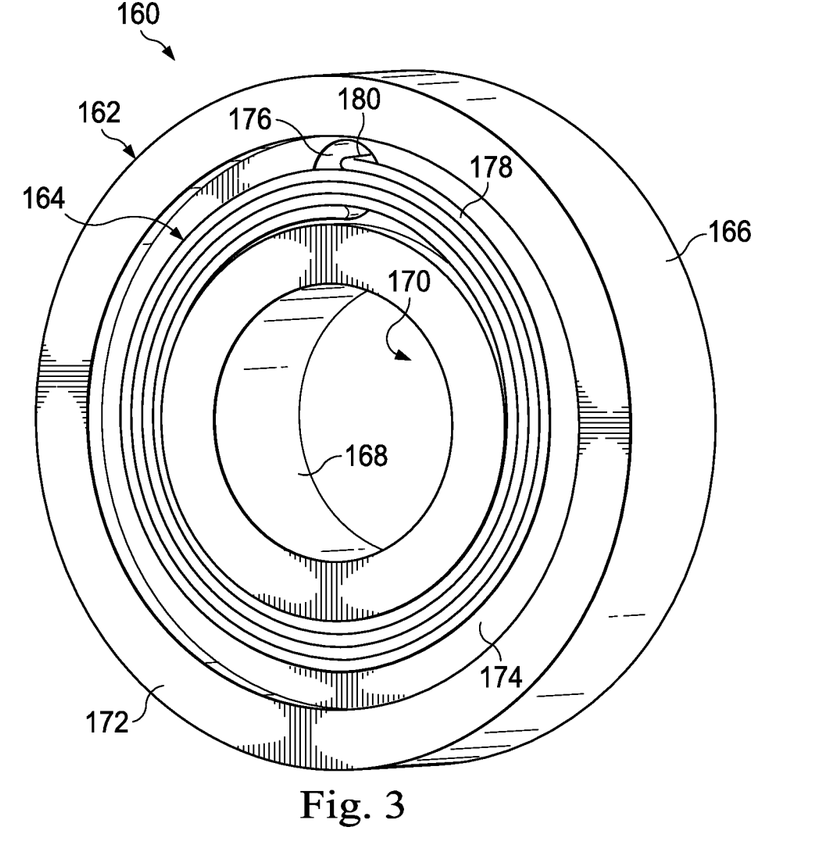
FIG. 3 is a diagrammatic perspective view of half of rotary transformer according to an embodiment of the present disclosure.
Figure 4:
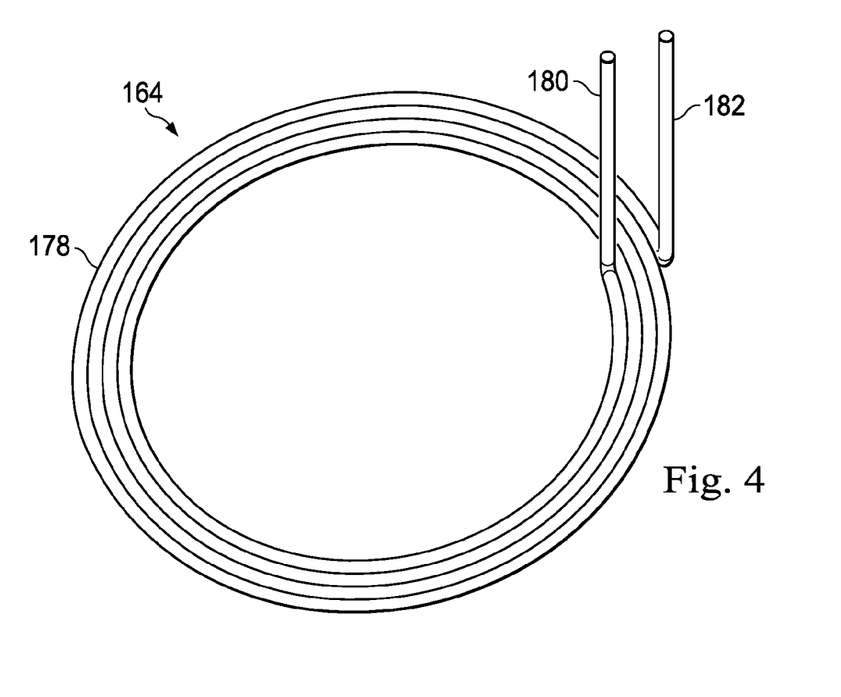
FIG. 4 is a diagrammatic perspective view of a coil of the half of the rotary transformer illustrated in FIG. 3 according to an embodiment of the present disclosure.
Figure 5:
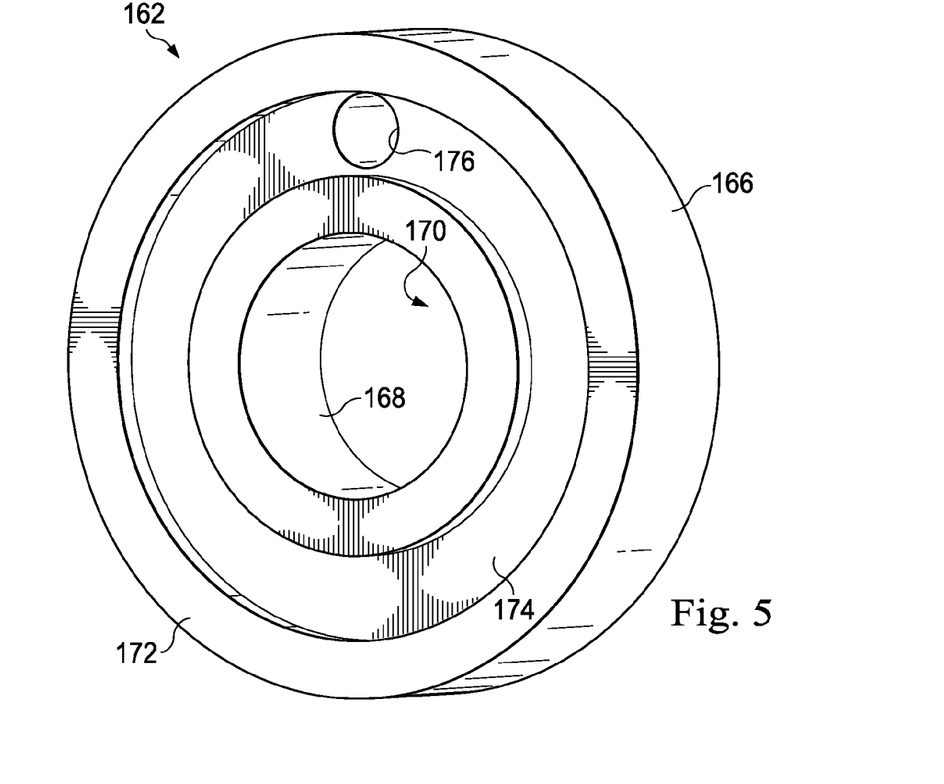
FIG. 5 is a diagrammatic perspective view of a core of the half of the rotary transformer illustrated in FIG. 3 according to an embodiment of the present disclosure.

Referring now to FIGS. 3 through 5, shown therein is a rotary transformer portion 160 according to an embodiment of the present disclosure. In that regard, the rotary transformer portion 160 generally represents half of a rotary transformer. Accordingly, in some instances, a pair of rotary transformer portions 160 is utilized to form a transformer, where one of the portions is arranged as the rotary portion and the other of the portions is arranged as the stationary portion. In that regard, it is understood that the rotary transformer portion 160 is suitable for use as either or both of the stationary portion and the rotating portion of a transformer. In some instances, a single rotary transformer portion 160 is used with another type of transformer portion having a different configuration to form a rotary transformer with two different halves. For example, one or more aspects related to the core and/or coil/winding of the two halves may be different.

As shown in FIG. 3, the rotary transformer portion 160 includes a core 162 and a coil 164. The core 162 is formed of a magnetically conductive material, such as ferrite. The core 162 may be formed of any suitable magnetically conductive material, which in some instances is made primarily of iron oxide ceramics with barium, nickel, and/or zinc added thereto. In the illustrated embodiment, the core 162 has cylindrical profile with an outer surface 166 with a circular cross-sectional profile. An inner surface 168 that is coaxial with the outer surface 166 defines a passage 170 through the core 162. As shown, the passage 170 extends generally coaxial and/or parallel with a central longitudinal axis of the core 162 associated with the cylindrical profile of the core. In some embodiments, the passage 170 is sized and shaped to receive a rotating element (e.g., a drive shaft, drive cable, drive extension, etc.) of an imaging device. Where the rotary transformer portion 160 is configured to be a rotary portion of a transformer, then the passage 170 is sized and shaped to facilitate fixedly securing the core 162 to the rotating element. In that regard, the core 162 is secured to the rotating element by mechanical connection, soldering, or with adhesive such as cyanoacrylate or epoxy. On the other hand, where the rotary transformer portion 160 is configured to be a stationary portion of a transformer, then the passage 170 is sized and shaped to facilitate passage of the rotating element through the core 162 in a manner that allows the rotating element to freely rotate with respect to the core 162. For example, the passage 170 may be larger than the diameter of the rotating element, include a lubricious coating, receive a bearing element, and/or combinations thereof to allow the rotating element to freely rotate with respect to the core 162.

The core 162 also includes a front surface 172. The front surface 172 includes a groove or recess 174. As shown, in the illustrated embodiment the recess 174 is an annular recess. In that regard, the front surface 172 includes a recessed surface portion that is recessed relative to surrounding portions of the front surface to define the recess 174. An opening 176 extends through the core 162 between the recessed surface portion of the front surface 172 and a back surface that is opposite the front surface. The coil 164 is coupled to the core 162 such that a coil portion 178 of the coil is positioned within the recess 174 in the front surface 172 of the core and leads 180 and 182 of the coil that extend from the coil portion 178 pass through the opening 176 to the back side of the core 162. As shown in FIG. 4, the leads 180 and 182 extend perpendicular to a plane defined by the coil portion 178. In that regard, the coil 164 of FIGS. 3 and 4 is illustrated as a wire coil formed of a single conductor wrapped to form the coil portion 178 with opposing ends of the conductor defining leads 180 and 182. However, in other instances the wire coil of FIGS. 3 and 4 is replaced by a flex circuit arrangement.

Figure 6:
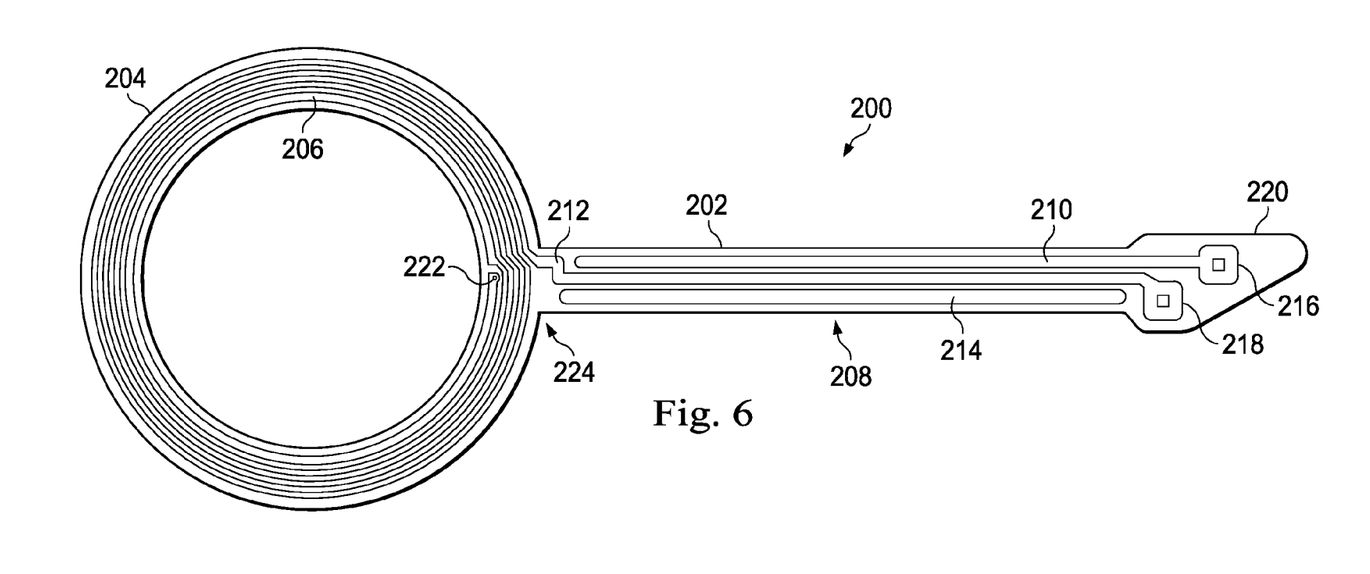
FIG. 6 is a diagrammatic top view of a flex circuit coil for a rotary transformer according to an embodiment of the present disclosure.

For example, referring now to FIG. 6, shown therein is a flex circuit 200 suitable for use as coil 164 of transformer portion 160 according to an embodiment of the present disclosure. In that regard, flex circuit 200 includes flexible substrate 202 onto which a plurality of conductive lines are formed. In that regard, the flexible substrate 202 may be formed of any suitable material, including without limitation polyimide, polyester, fluorinated ethylene propylene, polytetrafluoroethylene, and/or combinations thereof. Further, the conductive lines or circuitry formed on, in, and/or through the flexible substrate 202 may be any suitable conductive material, including without limitation copper, silver, gold, and/or combinations thereof. In that regard, the conductive lines and/or circuitry may be formed by various types of processes including deposition, sputtering, plating, and etching techniques employed in the fabrication of printed circuit boards, flexible printed circuits, microelectronic circuits, and/or semiconductors.

In the illustrated embodiment, the flexible substrate 202 of the flex circuit 200 includes a distal portion 204 onto which a set of coils or windings 206 are formed. In the illustrated embodiment, the set of coils 206 consists of four windings, but may have more or less windings in other configurations. In some instances, the distal portion 204 is sized and shaped to be received within the recess 174 of core 162 of FIG. 5. In that regard, the distal portion 204 is positioned within the recess of the core 162 such that the coils 206 face outward away from the recessed surface of the core 162. Further, the flexible substrate 202 includes an elongated extension 208 extending from the distal portion 204. A plurality of conductors 210, 212, and 214 extend along the length of the extension 208. In that regard, conductors 210 and 212 terminate in pads 216 and 218, respectively, at an end section 220 of the flex circuit 200. Pads 216 and 218 are utilized to communicatively couple the flex circuit 200 to additional components of an imaging system in some instances. For example, the pads 216 and 218 serve as solder points, in some instances, to electrically couple the circuitry of the flex circuit to additional circuitry of the imaging system. In that regard, in some instances the flex circuit 200 is coupled to a preamplifier or other processing component configured to condition signals provided by the flex circuit. As shown, conductor 212 is an extension of an outer portion of the coils 206 formed on the distal portion 204 of the flex circuit 200. An inner portion of the coils 206 is connected to the circuitry of the flex circuit by a via 222. In some instances, the via 222 is a blind via. In some embodiments, the via 222 facilitates connection of the inner portion of the coils 206 to circuitry on the backside of the flex circuit 200. One or more additional vias may be utilized to couple the circuitry on the back side of the flex circuit 200 to one or more of the conductors 210, 212, and 214 on the front side of the flex circuit, as shown in FIG. 6.

In some instances, the extension 208 is sized and shaped to extend through the opening 176 of core 162 of FIG. 5. In that regard, to allow the distal portion 204 to be seated within the recess 174 of the core 162, the flex circuit 200 is bent at the junction 224 between the distal portion 204 and the extension 208. In some instances, the bend is approximately 90 degrees such that distal portion 204 extends perpendicular to the extension 108. In such an orientation, the distal portion 204 of the flexible substrate 202 where the coils 206 are positioned extends in a plane that is perpendicular to a longitudinal plane of the elongated extension 208 of the flexible substrate.

Referring now to FIGS. 7-12, shown therein is a flex circuit 250 according to another embodiment of the present disclosure. Flex circuit 250 is also suitable for use as coil 164 of transformer portion 160. Flex circuit 250 includes flexible substrate onto which a plurality of conductive lines is formed. In that regard, the flexible substrate may be formed of any suitable material, including without limitation polyimide, polyester, fluorinated ethylene propylene, polytetrafluoroethylene, and/or combinations thereof. Further, the conductive lines or circuitry formed on, in, and/or through the flexible substrate may be any suitable conductive material, including without limitation silver, copper, gold, and/or combinations thereof. In that regard, the conductive lines and/or circuitry of the flex circuit 250 may be formed by various types of processes including deposition, sputtering, plating, and etching techniques employed in the fabrication of printed circuit boards, flexible printed circuits, microelectronic circuits, and/or semiconductors.

Figure 7:
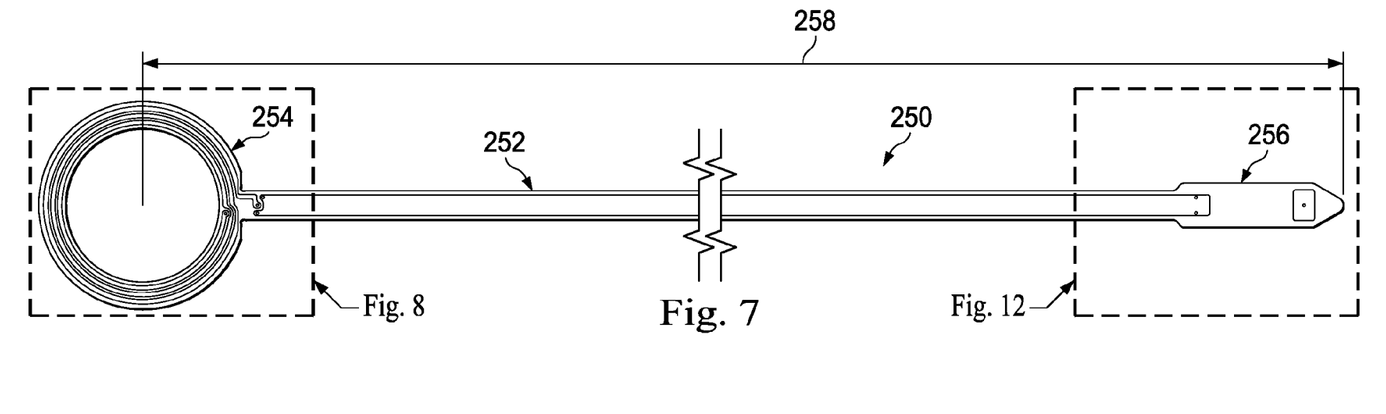
FIG. 7 is a diagrammatic top view of a flex circuit coil for a rotary transformer similar to that of FIG. 6, but illustrating another embodiment of the present disclosure.

Referring initially to FIG. 7, the flex circuit 250 includes an elongated body 252. A distal portion of the elongated body 252 is attached to a coil portion 254, while a proximal portion of the elongated body 252 is attached to a connection portion 256. In that regard, the elongated body 252, coil portion 254, and connection portion 256 are formed on a common flexible substrate in some instances. Accordingly, in some instances, the elongated body 252, coil portion 254, and connection portion 256 form a monolithic structure. As shown, the flex circuit 250 has a length 258 between the end of the connection portion 256 and a mid-point of the coil portion 254. Typically, the length 258 is between about 1 cm and about 12 cm, but may be shorter or longer for some particular embodiments. In that regard, the length 258 is selected based on the configuration of the device/system in which the transformer that the flex circuit 200 will be used. For example, in some instances, the length 258 is selected based on the distance between the transformer and the component(s) to which the flex circuit needs to be coupled.

Figure 8:
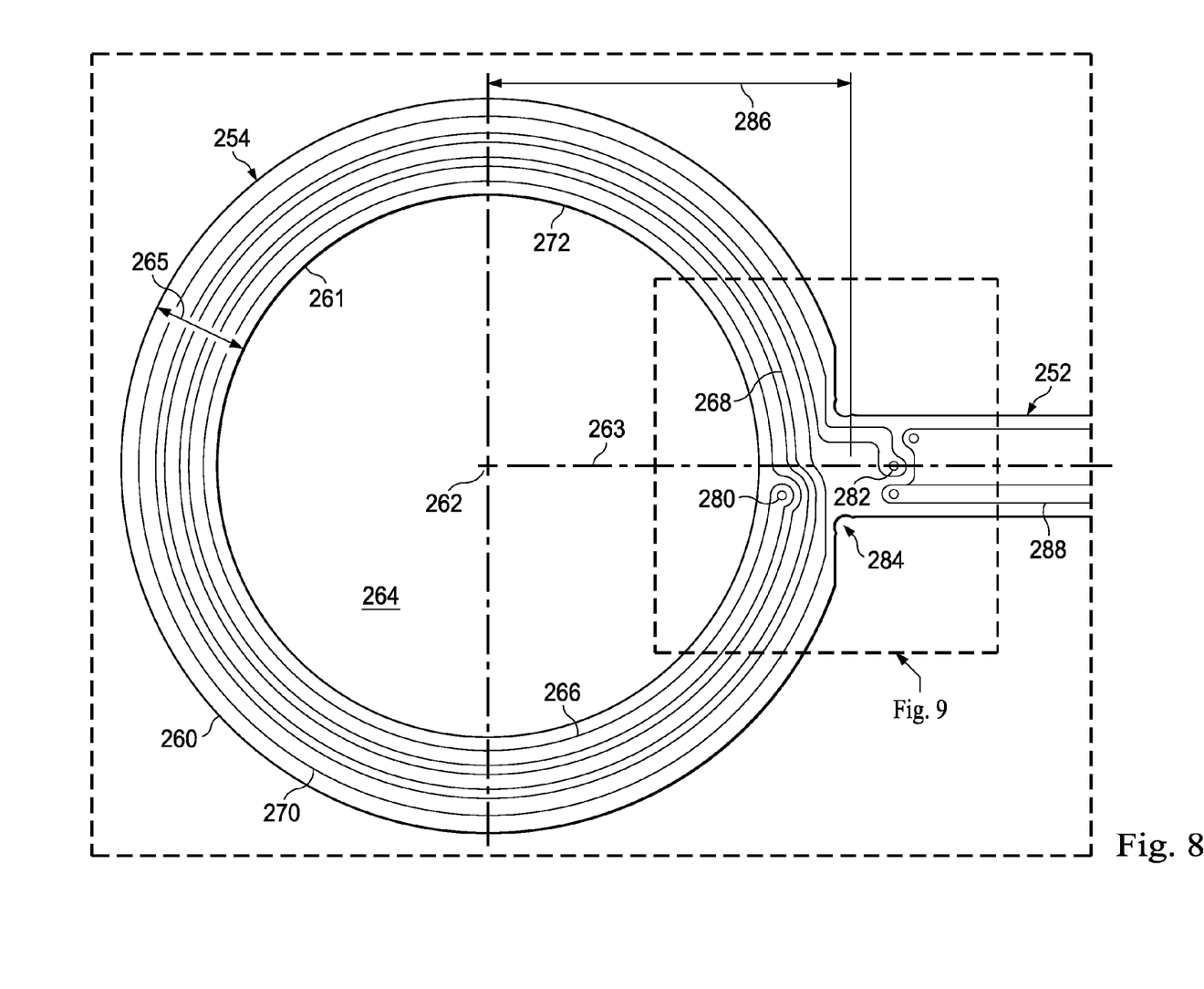
FIG. 8 is a diagrammatic close-up top view of a coil portion of the flex circuit coil illustrated in FIG. 7.
Figure 9:
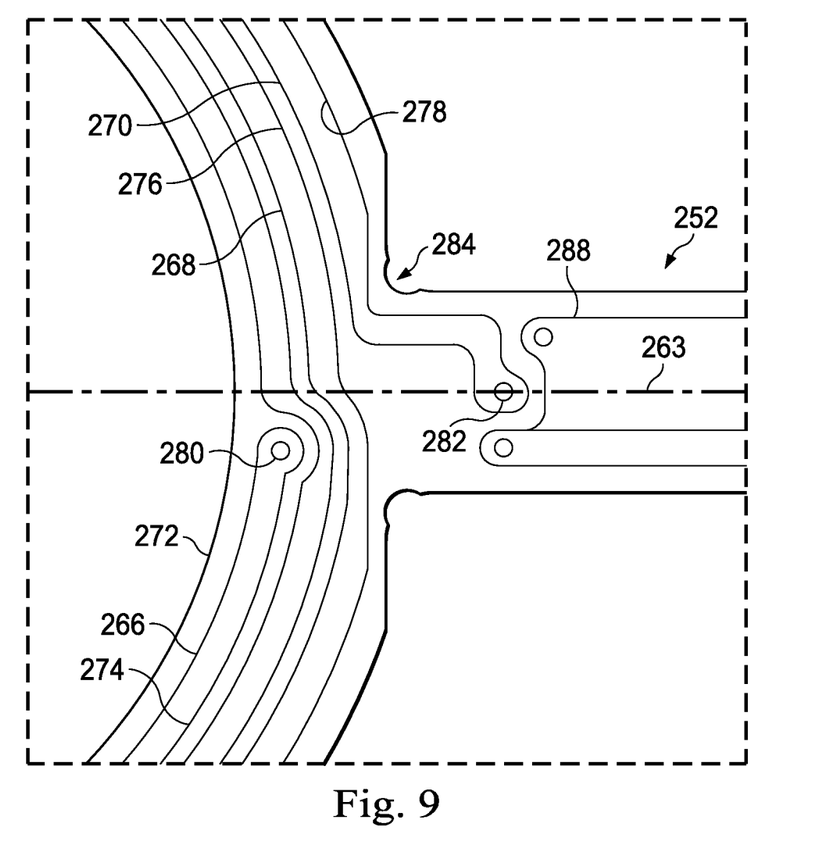
FIG. 9 is diagrammatic close-up top view of a transition between the coil portion of the flex circuit coil illustrated in FIG. 8 and an elongated substrate of the flex circuit coil.
Figure 10:
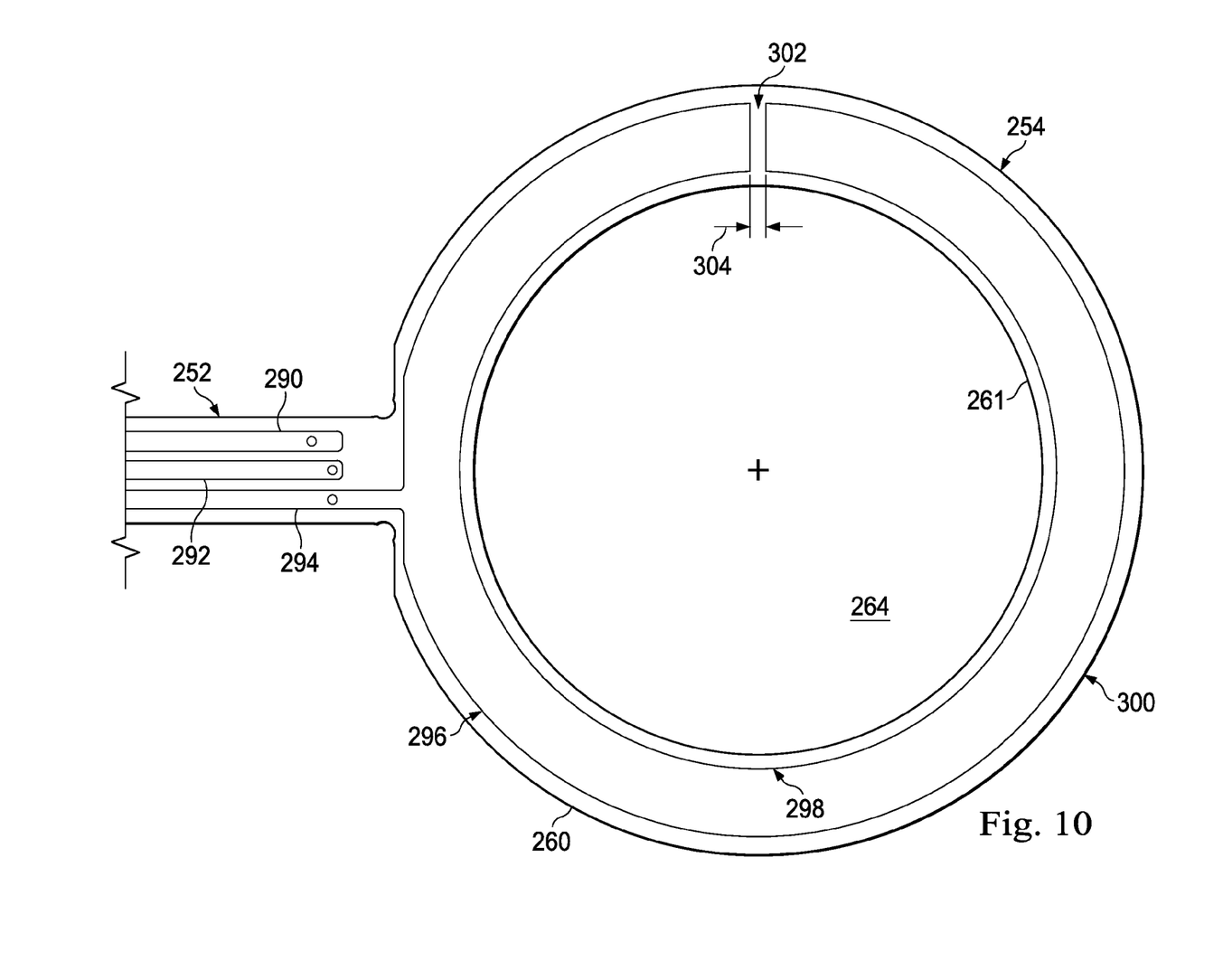
FIG. 10 is a diagrammatic close-up bottom view of the coil portion of the flex circuit coil illustrated in FIG. 8.

Referring now to FIGS. 8 and 9, shown therein are details of the coil portion 254 and the transition between the coil portion 254 and the elongated body 252. As shown in FIG. 8, the coil portion 254 has a generally circular outer boundary 260 and a circular inner boundary 261. The outer boundary 260 and the inner boundary 261 are centered about a center point 262 of the coil portion 254 that is aligned with a central longitudinal axis 263 of the elongated body 252 (when the coil portion 254 is not oriented perpendicular to the elongated body 252). The inner boundary 261 defines an opening 264 through the coil portion 254. As the outer boundary 260 and inner boundary 261 extend symmetrically about the center point 262 in the illustrated embodiment, the majority of the coil portion 254 has a width 265 between the outer boundary 260 and the inner boundary 261 that is equal to the difference in the radii of the outer boundary 260 and the inner boundary 261. In that regard, the inner boundary 261 has a radius between about 2 mm and about 5 mm, while the outer boundary 260 has a radius between about 3 mm and about 7 mm. As a result, the width 265 of the coil portion 254 is typically between about 0.5 mm and about 0.8 mm. It is understood that coil portion 254 may have other configurations, including other geometric profiles, other symmetrical profiles, non-geometric profiles, non-symmetrical profiles, and/or combinations thereof. The particular arrangement of the coil portion 254 is dictated based on the core into which it will be incorporated in some instances.

In the illustrated embodiment, the coil portion 254 has three windings 266, 268, and 270. In that regard, winding 266 is the inner-most winding, winding 268 is the middle winding, and winding 270 is the outer-most winding. As best shown in FIG. 9, the windings 266, 268, and 270 are separated by portions of the flexible substrate. In particular, portion 272 provides an inner boundary to winding 266, portion 274 separates winding 266 from winding 268, portion 276 separates winding 268 from winding 270, and portion 278 provides an outer boundary to winding 270. A blind via 280 connects winding 266 to circuitry on the backside of the flex circuit 250, while via 282 connects winding 270 to circuitry on the backside of the flex circuit 250. These connections will be discussed in further below. In some instances, a coating is formed over the windings 266, 268, and 270. In some instances, the coating is a Teflon layer having a thickness between about 0.05 mm (0.002") and about 0.08 mm (0.003"). In other instances, the coating is formed of polyimide, polyester, fluorinated ethylene propylene, polytetrafluoroethylene, and/or combinations thereof. In that regard, the coating may determine the distance between the windings of the stationary portion of the transformer and the rotating portion of the transformer. Accordingly, in some embodiments, to narrow the spacing between the windings of stationary and rotating portions down to less than 0.08 mm (0.003") or less than 0.05 mm (0.002") a coating is formed on only one of the stationary and rotating portions. In one particular embodiment, the coating is formed only on the stationary portion of the transformer.

In some instances, the coil portion 254 is sized and shaped to be received within the recess 174 of core 162 of FIG. 5, while the elongated body 252 is sized and shaped to extend through the opening 176 of core 162. In that regard, the coil portion 254 is positioned within the recess of the core 162 such that the windings 266, 268, and 270 face outward away from the recessed surface of the core 162. To allow the coil portion 254 to be seated within the recess 174 of the core 162 such that the windings 266, 268, and 270 face outward, the flex circuit 250 includes a junction 284 between the coil portion 254 and the elongated body 252 that is configured to be bent at approximately a 90 degree angle such that the coil portion 254 extends perpendicular to the elongated body 252. In such an orientation, the coil portion 254 of the flexible circuit 250 extends in a plane that is perpendicular to a longitudinal plane of the elongated body 252. As shown in FIG. 8, the junction 284 is spaced from the center point 262 of the coil portion 254 by a distance 286. Generally, the distance 286 is approximately equal to the radius of the outer boundary 260, but is greater than or less than the radius of the outer boundary in some instances.

As shown in FIGS. 8 and 9, the front side of the flex circuit 250 includes a shield 288, in some instances, that extends along a length of the elongated body 252. Generally, the shield 288 is configured to help limit and/or prevent electromagnetic interference from adversely affecting the circuitry of the flex circuit 250. Accordingly, in some instances, the shield 288 is connected to the ground plane of the circuit. Further, the shield 288 is formed of a conductive material(s) similar to that of the leads or traces. Accordingly, in some embodiments the shield 288 is formed of silver, copper, gold, and/or combinations thereof. In that regard, the shield 288 is configured to protect circuitry on the backside of the flex circuit 250 from electromagnetic interference (EMI) in some instances. For example, referring now to FIGS. 10 and 11, in the illustrated embodiment the flex circuit 250 includes conductors 290, 292, and 294 that extend along the length of the elongated body 252 to the connection portion 256. As shown in FIG. 12, the shield 288 also extends along the length of the elongated body 252 to the connection portion 256 to protect the conductors 290, 292, and 294 from electromagnetic interference. The shield 288 also helps to limit electromagnetic interference caused by the conductors 290, 292, and 294 on other components of the imaging device or system. In some instances, the circuitry of the flex circuit 250 is arranged as a microstrip, grounded coplanar waveguide, or stripline. In that regard, in some embodiments, conductors 288, 290, and/or 294 serve as a shields or grounds.

As noted above with respect to FIGS. 8, 9, and 10, a blind via 280 connects the winding 266 on the front side of the coil portion 254 of the flex circuit 250 to circuitry on the back side of the flex circuit. In the illustrated embodiment, the blind via 280 connects the winding 266 to a shield 296 that is positioned on the back side of the coil portion 254 of the flex circuit 250. In that regard, the shield 296 is electrically coupled to conductor 294. In some instances, the shield 296 and the conductor 294 are integrally formed. As shown, the shield 296 is separated from the outer and inner boundaries 260, 261 of the coil portion 254 by portions of the flexible substrate. In particular, portion 298 provides an inner boundary to the shield 296, while portion 300 provides an outer boundary to the shield. Further, in the illustrated embodiment the shield 296 extends circumferentially around the vast majority of the coil portion 254. However, the shield 296 does not extend all the way around the coil portion 254. Rather, as shown, a gap 302 is formed to interrupt the loop that would otherwise be created around the coil portion 254 by the shield 296. Gap 302 prevents current from circulating around the shield 296 as would occur if the shield was formed as complete loop. Such undesirable circulating current would likely dampen the magnetic field that is required for efficient transducer coupling. Gap 302 has width 304 that is generally about 0.08 mm (0.003") for the frequencies utilized for IVUS imaging, but may be larger or smaller in other instances. As also noted above with respect to FIGS. 8 and 9, a via 282 connects the winding 270 on the front side of the coil portion 254 of the flex circuit 250 to circuitry on the back side of the flex circuit. In the illustrated embodiment, the via 282 connects the winding 270 to conductor 292 that is positioned on the back side of the flex circuit 250.

Figure 11:
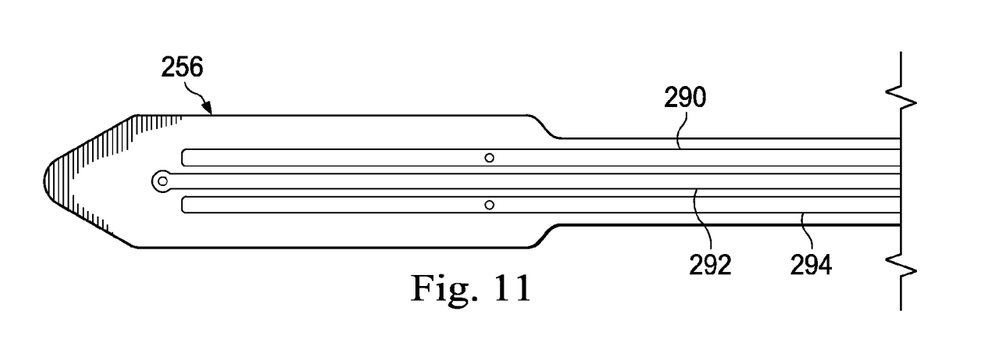
FIG. 11 is a diagrammatic close-up top view of an end portion of the elongated substrate of the flex circuit coil.
Figure 12:
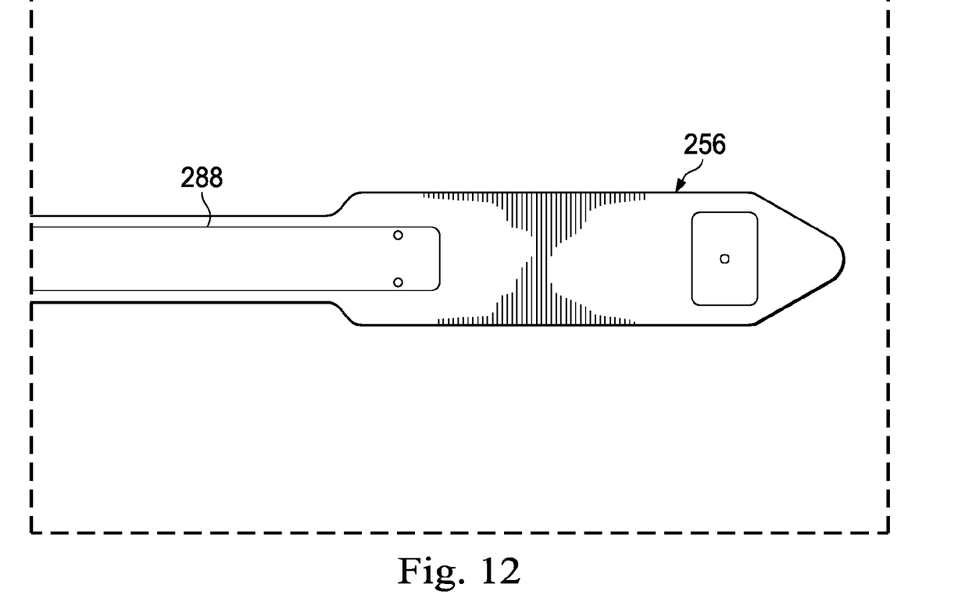
FIG. 12 is a diagrammatic close-up bottom view of the end portion of the elongated substrate of the flex circuit coil illustrated in FIG. 11.

As shown in FIGS. 11 and 12, the conductors 290, 292, and 294, as well as shield 288, terminate at the connection portion 256 of the flex circuit 250. In that regard, connection portion 256 is configured to couple the flex circuit 250 to additional components of an imaging system in some instances. For example, the connection portion 256 serves as a solder point(s), in some instances, to electrically couple the circuitry of the flex circuit 250 to additional circuitry of the imaging system. In that regard, in some instances the flex circuit 250 is coupled to a preamplifier or other processing component configured to condition signals provided by the flex circuit 250 for output to another component, such as a patient interface module or coupled to the cable connected to the transducer. In some embodiments, instead of utilizing one or both of shields 288 and 296 discussed with respect to FIGS. 8 through 10, the transformer is positioned within a shielded housing that protects the transformer and its component from electromagnetic interference.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A rotary transformer for a rotational intravascular ultrasound (IVUS) device, the rotary transformer comprising:
  a rotational component configured to be fixedly secured to a rotating portion of the rotational IVUS device such that the rotational component rotates with the rotating portion of the rotational IVUS device, the rotational component including:
  a core having a front surface with a recess and an opening extending through the core from the recess to a back surface; and
  a flex circuit coupled to the core such that a coil portion of the flex circuit is received within the recess of the front surface of the core; and
  a stationary component positioned adjacent to the rotational component such that when the rotational component rotates with the rotating portion of the rotational IVUS device the rotational component rotates relative to the stationary component, the stationary component including:
  a core; and
  a coil coupled to the core;
  wherein the coil portion of the flex circuit of the rotational component and the coil of the stationary component are configured to inductively communicate signals between one another.

2. The rotary transformer of claim 1, wherein an elongated extension of the flex circuit extends through the opening of the core of the rotational component.

3. The rotary transformer of claim 2, wherein the core of the stationary component has a front surface and a back surface, wherein the front surface includes a recess, wherein an opening extends through the core of the stationary component from the recess to the back surface.

4. The rotary transformer of claim 3, wherein the coil of the stationary component is received within the recess of the core of the stationary component and leads coupled to the coil extend through the opening extending through the core of the stationary component.

5. The rotary transformer of claim 4, wherein the coil of the stationary component is formed on a coil portion of a flex circuit and wherein the leads are formed on an elongated extension of the flex circuit extending from the coil portion.

6. The rotary transformer of claim 1, wherein the coil portion of the flex circuit extends in a plane that is perpendicular to a longitudinal plane of the elongated extension.

7. The rotary transformer of claim 1, wherein the coil portion of the flex circuit includes a front surface and a back surface, wherein a coil is formed by the front surface of the flex circuit and wherein the back surface of the flex circuit is positioned against the recess of the core.

8. The rotary transformer of claim 7, wherein the back surface of the flex circuit includes a shield.

9. The rotary transformer of claim 8, wherein at least one gap is formed in the shield to prevent current from being induced in the shield.

10. The rotary transformer of claim 7, wherein the coil is connected to circuitry that extends along the elongated extension of the flex circuit.

11. The rotary transformer of claim 10, wherein an inner portion of the coil is connected to a first lead extending along a back surface of the elongated extension of the flex circuit.

12. The rotary transformer of claim 11, wherein a blind via connects the inner portion of the coil to the first lead.

13. The rotary transformer of claim 11, wherein an outer portion of the coil is connected to a second lead extending along a back surface of the elongated extension of the flex circuit.

14. The rotary transformer of claim 13, wherein a via connects the outer portion of the coil to the second lead.

15. The rotary transformer of claim 13, wherein a shield extends along a majority of the elongated extension of the flex circuit on a front surface of the elongated extension opposite the back surface.

16. The rotary transformer of claim 13, wherein the circuitry extending along the elongated extension of the flex circuit, including the first and second leads, is arranged as a microstrip, grounded coplanar waveguide, or stripline.

17. The rotary transformer of claim 1, wherein the cores of the rotational and stationary components have a cylindrical profile.

18. The rotary transformer of claim 17, wherein the opening in the core of the rotational component extends parallel to a longitudinal axis of the core.

19. The rotary transformer of claim 18, wherein the core of the rotational component further includes a central passage configured to receive the rotating portion of the rotational IVUS device.

20. The rotary transformer of claim 19, wherein the central passage is configured to receive a drive shaft or drive cable of the rotational IVUS device.

21. The rotary transformer of claim 19, wherein the recess is positioned symmetrically about the central passage.

22. A method, comprising:
providing a first core formed of a magnetically conductive material, the first core having a front surface and a back surface, wherein the front surface includes a recess, wherein an opening extends through the first core from the recess to the back surface;
providing a first flex circuit including a coil portion and an elongated extension extending from the coil portion; and
coupling the first flex circuit to the first core such that the coil portion of the first flex circuit is received within the recess of the front surface of the first core.

23. The method of claim 22, wherein the coupling the first flex circuit to the first core includes extending the elongated extension through the opening extending through the first core.

24. The method of claim 23, further comprising:
providing a second core formed of a magnetically conductive material, the second core having a front surface and a back surface, wherein the front surface includes a recess, wherein an opening extends through the second core from the recess to the back surface;
providing a second flex circuit including a coil portion and an elongated extension extending from the coil portion;
coupling the second flex circuit to the second core such that the coil portion of the second flex circuit is received within the recess of the front surface of the second core and the elongated extension extends through the opening extending through the second core from the recess to the back surface; and
positioning the first core with the first flex circuit coupled thereto adjacent the second core with the second flex circuit coupled thereto such that the front surface of the first core faces the front surface of the second core.

25. The method of claim 24, further comprising:
fixedly securing the first core to a rotational element of an imaging device such that the first core rotates with respect to the second core when the rotational element is rotated.

26. The method of claim 25, wherein fixedly securing the first core to the rotational element comprises extending a first portion of the rotational element through a passage extending through the first core.

27. The method of claim 26, further comprising extending a second portion of the rotational element through a passage extending through the second core.

* * * * *